US012582329B2

(12) United States Patent
Speck et al.

(10) Patent No.: US 12,582,329 B2
(45) Date of Patent: Mar. 24, 2026

(54) MAGNETO-MECHANICAL CAPSULES

(71) Applicant: Northern Digital Inc., Waterloo (CA)

(72) Inventors: Robin Speck, Villingen-Schwenningen (DE); Anja Bauer, Allensbach (DE); Christian Schilling, Thayngen (CH); Scott Garth Illsley, Stratford (CA)

(73) Assignee: Northern Digital Inc., Waterloo (CA)

( * ) Notice: Subject to any disclaimer, the term of this patent is extended or adjusted under 35 U.S.C. 154(b) by 0 days.

(21) Appl. No.: 18/925,449

(22) Filed: Oct. 24, 2024

(65) Prior Publication Data

US 2025/0127417 A1     Apr. 24, 2025

Related U.S. Application Data

(60) Provisional application No. 63/545,503, filed on Oct. 24, 2023.

(51) Int. Cl.
A61B 5/00          (2006.01)
A61B 5/06          (2006.01)

(52) U.S. Cl.
CPC ...... A61B 5/062 (2013.01); A61B 2562/0223 (2013.01)

(58) Field of Classification Search
CPC ................................ A61B 1/041; A61B 5/062
See application file for complete search history.

(56) References Cited

U.S. PATENT DOCUMENTS

| | | |
|---|---|---|
| 11,598,677 B2 | 3/2023 | Gleich et al. |
| 11,774,300 B2 | 10/2023 | Gleich et al. |

| | | | |
|---|---|---|---|
| 2005/0216231 A1 | 9/2005 | Aoki et al. | |
| 2009/0001969 A1 | 1/2009 | Berkcan | |
| 2010/0001592 A1* | 1/2010 | Kawano | A61B 34/72 |
| | | | 310/12.14 |
| 2011/0207998 A1* | 8/2011 | Katayama | A61B 1/041 |
| | | | 600/106 |
| 2020/0397320 A1 | 12/2020 | Gleich et al. | |
| 2020/0397510 A1 | 12/2020 | Gleich et al. | |
| 2020/0397530 A1 | 12/2020 | Gleich et al. | |
| 2020/0400509 A1 | 12/2020 | Gleich et al. | |
| 2021/0244305 A1 | 8/2021 | Gleich et al. | |
| 2022/0257138 A1 | 8/2022 | Gleich et al. | |

FOREIGN PATENT DOCUMENTS

WO        WO 2018/183949 A1        10/2018

OTHER PUBLICATIONS

[No Author Listed], "Electromagnetic Tracking Education Guide," Northern Digital Inc., Aug. 2021, 12 pages.
Hu et al., "Locating Intra-Body Capsule Object by Three Magnet Sensing System," IEEE Sensors Journal, Jul. 1, 2016, 16(13): 5167-5176.
Written Opinion in International Appln. No. PCT/IB2024/060492, mailed on Apr. 8, 2025, 6 pages.
International Search Report and Written Opinion in International Appln. No. PCT/IB2024/060492, mailed on Apr. 8, 2025, 13 pages.

* cited by examiner

*Primary Examiner* — Rajeev P Siripurapu
(74) *Attorney, Agent, or Firm* — Fish & Richardson P.C.

(57)                ABSTRACT

Magneto-mechanical capsules can include a body, a first magnet attached to a first end of the body, a second magnet attached to a second end of the body, and a third magnet disposed between the first magnet and the second magnet. In some cases, the third magnet is configured to oscillate in response to an external magnetic field to produce a second magnetic field.

18 Claims, 10 Drawing Sheets

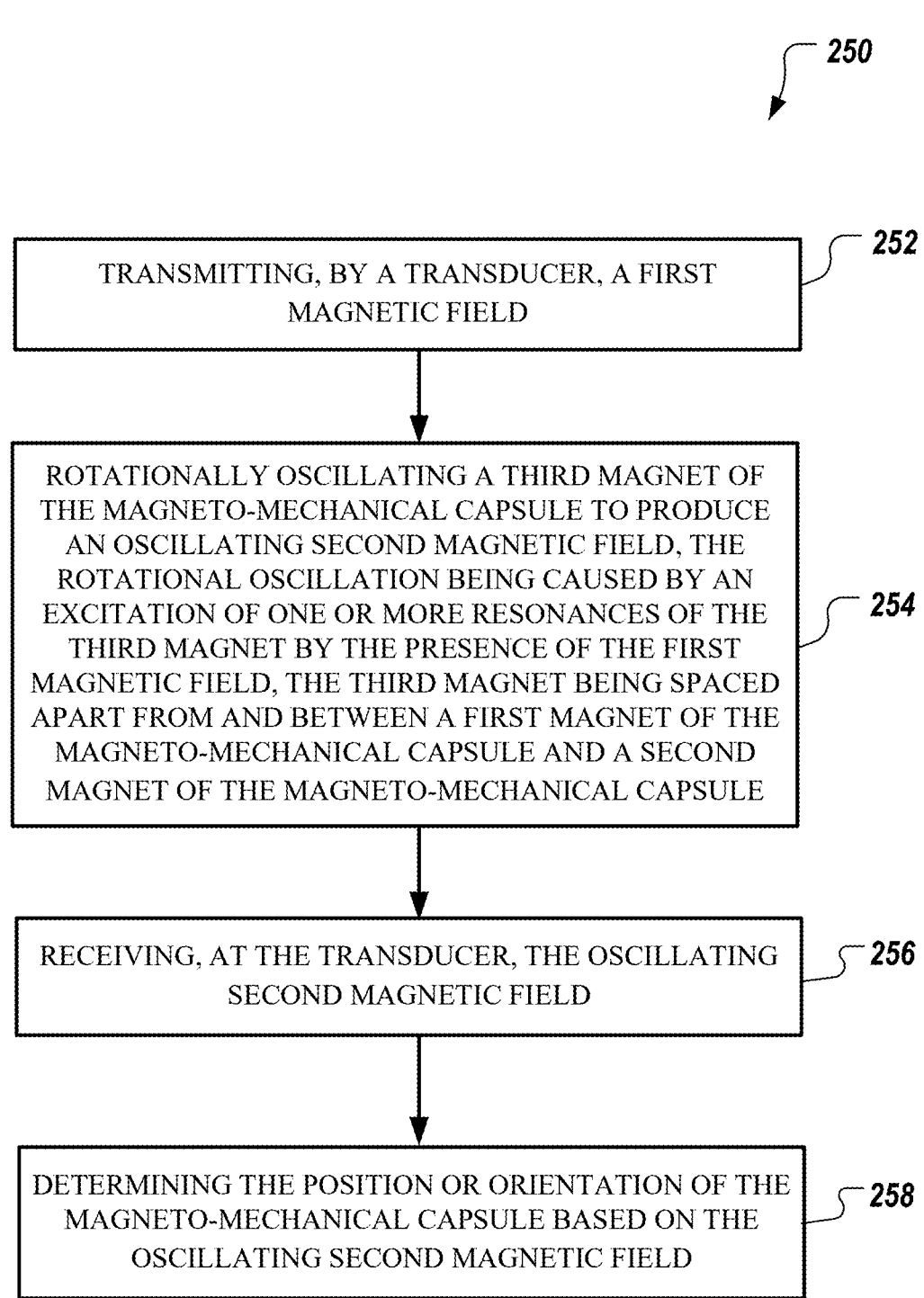

*250*

*252*

TRANSMITTING, BY A TRANSDUCER, A FIRST MAGNETIC FIELD

*254*

ROTATIONALLY OSCILLATING A THIRD MAGNET OF THE MAGNETO-MECHANICAL CAPSULE TO PRODUCE AN OSCILLATING SECOND MAGNETIC FIELD, THE ROTATIONAL OSCILLATION BEING CAUSED BY AN EXCITATION OF ONE OR MORE RESONANCES OF THE THIRD MAGNET BY THE PRESENCE OF THE FIRST MAGNETIC FIELD, THE THIRD MAGNET BEING SPACED APART FROM AND BETWEEN A FIRST MAGNET OF THE MAGNETO-MECHANICAL CAPSULE AND A SECOND MAGNET OF THE MAGNETO-MECHANICAL CAPSULE

*256*

RECEIVING, AT THE TRANSDUCER, THE OSCILLATING SECOND MAGNETIC FIELD

*258*

DETERMINING THE POSITION OR ORIENTATION OF THE MAGNETO-MECHANICAL CAPSULE BASED ON THE OSCILLATING SECOND MAGNETIC FIELD

FIG. 6

MAGNETO-MECHANICAL CAPSULES

CLAIM OF PRIORITY

This application claims priority under 35 USC § 119(e) to U.S. Patent Application Ser. No. 63/545,503, filed on Oct. 24, 2023, the entire contents of which are hereby incorporated by reference.

TECHNICAL FIELD

The present disclosure relates to magneto-mechanical capsules and tracking systems that determine a position and/or orientation of magneto-mechanical capsules within a patient based on an emitted electro-magnetic field from the magneto-mechanical capsules.

BACKGROUND

It is often desirable to track markers within an anatomy of a patient to diagnose medical conditions. Some techniques include imaging (e.g., an angiogram, ultrasound, tomography, etc.) to track the markers. Other techniques use electro-magnetic sensors to track the markers. For example, an electro-magnetic sensor can detect an electric or magnetic field generated by a marker and determine the position of the marker based on the detected electric or magnetic field.

SUMMARY

Magneto-mechanical capsules are devices that receive energy from an external magnetic field and do not need a wired connection to an energy supply. The magneto-mechanical capsules described herein include at least two fixed magnets and at least one free (e.g., non-fixed) magnet arranged in mechanical equilibrium with each other. In the presence of an external (or first) electro-magnetic field generated by a transmitter, the free magnet oscillates relative to the fixed magnets at one or more resonant frequencies to produce a second electro-magnetic field. After turning off the electro-magnetic field, the free magnet keeps oscillating and therefore keeps emitting an oscillating electro-magnetic field. This second electro-magnetic field is sensed by a receiver and a computer system can determine a position, orientation, etc. of the magneto-mechanical capsule based on one or more signals representing the oscillating electro-magnetic field. Details about magneto-mechanical markers are described in U.S. Pat. Nos. 11,598,677 and 11,774,300, which are hereby incorporated in their entirety.

Low friction between the oscillating magnet and objects in contact with the oscillating magnet is important. Low friction helps to provide a long and measurable oscillation after turning off the external electro-magnetic field. In some examples, three magnets are used (e.g., the free magnet is disposed between and spaced apart from the two fixed magnets) to reduce friction caused by magnetic attraction. In this case, the oscillating magnet faces very low magnetic attraction.

In an aspect, a magneto-mechanical capsule includes a body, a first magnet attached to a first end of the body, a second magnet attached to a second end of the body, and a third magnet disposed between the first magnet and the second magnet. In some cases, the third magnet is configured to oscillate in response to an external magnetic field to produce a second magnetic field.

In some implementations, the third magnet is disposed equidistantly between the first magnet and the second magnet.

In some implementations, the third magnet is configured to oscillate about a longitudinal axis of the body in response to the external magnetic field.

In some implementations, the magneto-mechanical capsule includes a stabilizer disposed within the body. The stabilizer is configured to limit a rotation of the third magnet about an axis perpendicular to the longitudinal axis.

In some implementations, the stabilizer includes (i) a first pin extending in a longitudinal direction from the third magnet and having an end that is disposed within a cavity of the first magnet and (ii) a second pin extending in an opposite longitudinal direction from the third magnet and having an end that is disposed within a cavity of the second magnet.

In some implementations, the cavity is very small or not present at all. In this case, the pins limit any movement of the third magnet in the longitudinal direction. The rotation of the third magnet around longitudinal axis can be limited by a bushing or by the sidewalls of a surrounding cylinder defining the body.

In some implementations, the respective ends of the first and second pins are configured to move within the respective cavities of the first and second magnets in response to the external magnetic field.

In some implementations, the first and second pins are configured to limit the rotation of the third magnet about the axis perpendicular to the longitudinal axis by contacting respective sidewalls of the respective cavities.

In some implementations, the stabilizer includes a bushing disposed circumferentially around the third magnet.

In some implementations, the bushing is in slidable contact with at least one of the first magnet, the second magnet, or a sidewall of the body.

In some implementations, the bushing is configured to limit the rotation of the third magnet about the axis perpendicular to the longitudinal axis by limiting an axial movement of the third magnet within the body. In some implementations, the bushing is configured to limit an axial movement of the third magnet within the body.

In some implementations, the first magnet, the second magnet, and the third magnet are disc-shaped and are concentrically disposed along a longitudinal axis of the body. In some implementations, the first magnet, the second magnet, and the third magnet are other shapes such as diamond-shaped, square-shaped, oval-shaped, etc.

In some implementations, the first magnet has (i) a north pole arranged on a first side of the longitudinal axis of the body and (ii) a south pole arranged on a second side of the longitudinal axis of the body.

In some implementations, the north and south poles of the first magnet are arranged in the same direction as north and south poles of the second magnet.

In some implementations, the north and south poles of the third magnet are arranged in an opposite direction to the north and south poles of the first and second magnets.

In some implementations, the body has a length between 0.5 and 2.0 mm and a diameter between 0.1 mm and 0.8 mm.

In an aspect, a system includes a transducer and a magneto-mechanical capsule. The transducer is configured to transmit a first magnetic field. The magneto-mechanical capsule includes a body, a first magnet attached to a first end of the body, a second magnet attached to a second end of the body, and a third magnet disposed between the first magnet and the second magnet, the third magnet configured to oscillate in response to the first magnetic field and produce a second magnetic field. The transducer is configured to receive the second magnetic field.

In some implementations, the system includes a processor configured to determine a position or orientation of the magneto-mechanical capsule based on the received second magnetic field.

In some implementations, the transducer is configured to receive the second magnetic field after stopping the transmission of the first magnetic field.

In an aspect, a method for determining a position or orientation of a magneto-mechanical capsule includes: transmitting, by a transducer, a first magnetic field; rotationally oscillating a third magnet of the magneto-mechanical capsule to produce an oscillating second magnetic field, the rotational oscillation being caused by an excitation of one or more resonances of the free magnet by the presence of the first magnetic field, the free magnet being spaced apart from and between a first magnet of the magneto-mechanical capsule and a second magnet of the magneto-mechanical capsule; receiving, at the transducer, the oscillating second magnetic field; and determining the position or orientation of the magneto-mechanical capsule based on the oscillating second magnetic field.

In some implementations, the method includes stopping the transmitting of the first magnetic field after rotationally oscillating the third magnet of the magneto-mechanical capsule and before receiving the oscillating second magnetic field.

In some implementations, the method is performed the method is performed while the magneto-mechanical capsule is inserted into a patient such that the determined position of the magneto-mechanical capsule represents a position of the magneto-mechanical capsule within the patient.

The magneto-mechanical capsules described herein include one or more of the following advantages.

In some implementations, magneto-mechanical capsules that have a third magnet suspended in air between the first and second magnets improve the manufacturability of the magneto-mechanical capsules because a thin tether or filament to support one of the magnets, which is generally difficult to manufacture, is not necessary. It can sometimes be difficult to reliability attach thin filaments to magnets in a manner that allows them to oscillate in the presence of an external magnetic field while minimizing friction and contact with other components within the capsule while providing a signal that can be sensed by one or more sensors.

In some implementations, magneto-mechanical capsules that include the stabilizers described herein have decreased wobbling of the magnets. Decreasing the wobbling generally results in increased position and orientation detection of the magneto-mechanical capsules.

In some implementations, magneto-mechanical capsules that include magnets in the form of disc-shaped cylinders have an increased influence on the external magnetic field. This is because having disc-shaped cylinders that take the form of the body of the magneto-mechanical capsules generally maximize an amount of magnetic material that can fit inside the magneto-mechanical capsules. This generally results in more accurate position and orientation detection of the magneto-mechanical capsules.

In some implementations, magneto-mechanical capsules that include one or more stabilizers can be easier to assembly than magneto-mechanical capsules without stabilizers because it helps to position the free magnet within the stack in its mechanical equilibrium state such that does not "snap" onto one of the two fixed magnets.

The details of one or more implementations are set forth in the accompanying drawings and the description herein. Other features, objects, and advantages will be apparent from the description and drawings, and from the claims.

DESCRIPTION OF THE DRAWINGS

FIG. 6 is a flowchart of a method that uses the magneto-mechanical capsule of FIG. 1.

Like reference numbers represent corresponding parts throughout.

DETAILED DESCRIPTION

Figure 1:
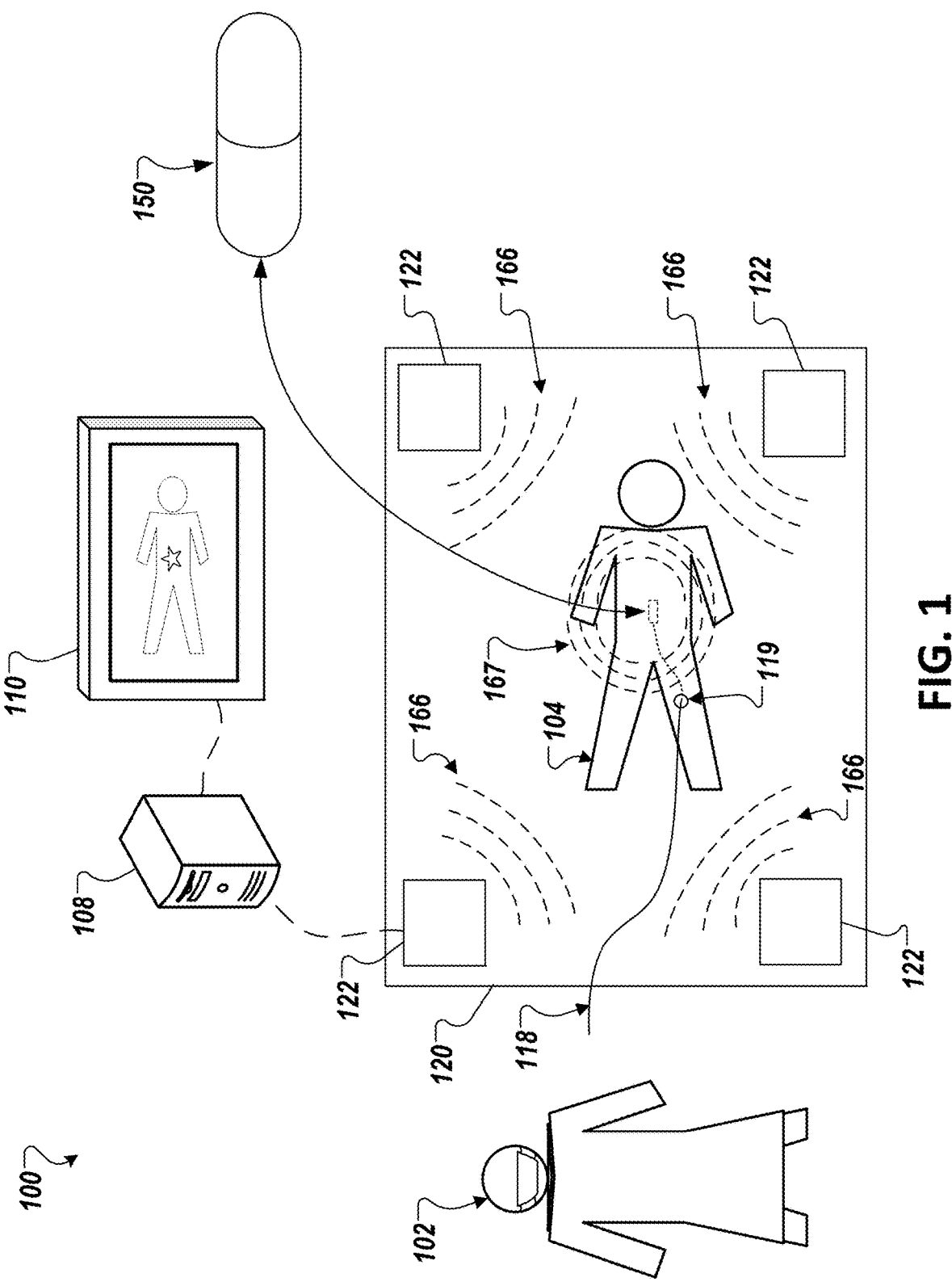
FIG. 1 shows a magneto-mechanical capsule being used in a medical environment.

FIG. 1 shows a medical environment 100 where a medical professional 102 desires to know the position and/or orientation of a magneto-mechanical capsule 150 within the anatomy of a patient 104 during a medical procedure (e.g., a minimally invasive procedure). For example, in the example represented in FIG. 1, the medical professional 102 has inserted a catheter 118 into the patient 104 via an insertion site 119. One or more magneto-mechanical capsules 150 are arranged on the catheter 118. In this example, a single magneto-mechanical capsule 150 is used, but in some examples, a plurality (e.g., 2-10) of magneto-mechanical capsules 150 are arranged on the catheter 118.

The patient 104 is laying on a bed 120 with a plurality of electro-magnetic transducers 122 embedded in the bed 120. Each of the transducers 122 are connected to a computer system 108 and generally include one or more coils to produce and transmit an electro-magnetic field 166. Each transducer 122 is arranged to produce the electro-magnetic field 166 in the vicinity of the patient 104. The transducers 122 can be configured to operate in both a transmit mode to transmit the electro-magnetic field 166 and in a receive mode to receive an electro-magnetic field 167.

In some implementations, each transducer 122 produces a different electro-magnetic field 166 so that distances and orientations between the magneto-mechanical capsule 150 and the respective transducers 122 can be determined by the computer system 108. In some examples, the computer system 108 controls the transducers 122 by controlling them on and off so that only one of the transducers 122 is transmitting an electro-magnetic field 166 at a given time. While the transducers 122 are embedded in the bed 120 in this example, in some implementations, the transducers 122 are embedded elsewhere (e.g., in a C-arm machine).

When the transducers 122 are in receive mode, the transducers 122 sense electro-magnetic field 167 produced by the magneto-mechanical capsule 150. Details regarding how the magneto-mechanical capsule 150 produces the electro-magnetic field 167 is described with reference to FIG. 3. The received electro-magnetic field 167 is then processed by the computer system 108 to determine the position and/or orientation of the magneto-mechanical capsule 150 within the anatomy of the patient 104 (or wherever the magneto-mechanical capsule 150 is used).

In some cases, the computer system 108 controls a display 110 to present a representation of the determined position, orientation, etc. of the magneto-mechanical capsule 150 within the anatomy of the patient 104. The computer system 108 includes one or more processors to determine the position and/or orientation of the magneto-mechanical capsule 150 within the anatomy of the patient 104 and control the display 110. In some implementations, the computer system 108 includes one or more components of a computer device 400 or an example mobile computer device 450 described with reference to FIG. 16. Details regarding how the computer system 108 determines the position and orientation of the magneto-mechanical capsule 150 is described with reference to FIGS. 3-6.

Preferably, the magneto-mechanical capsule 150 is relatively small (e.g., typically on the order of millimeters (mm)). In some implementations, the magneto-mechanical capsule 150 can employ one or more geometries (e.g., pill-shaped, cylindrical, square, oval, etc.). In some implementations, the magneto-mechanical capsule 150 is cylindrical and has a length between 0.5 and 2.0 mm and a diameter between 0.1 mm and 0.8 mm. These dimensions allow the capsule 150 to be embedded in medical instruments (e.g., the catheter 118) to assist in determining the position and/or orientation of the medical instrument.

Figure 2:
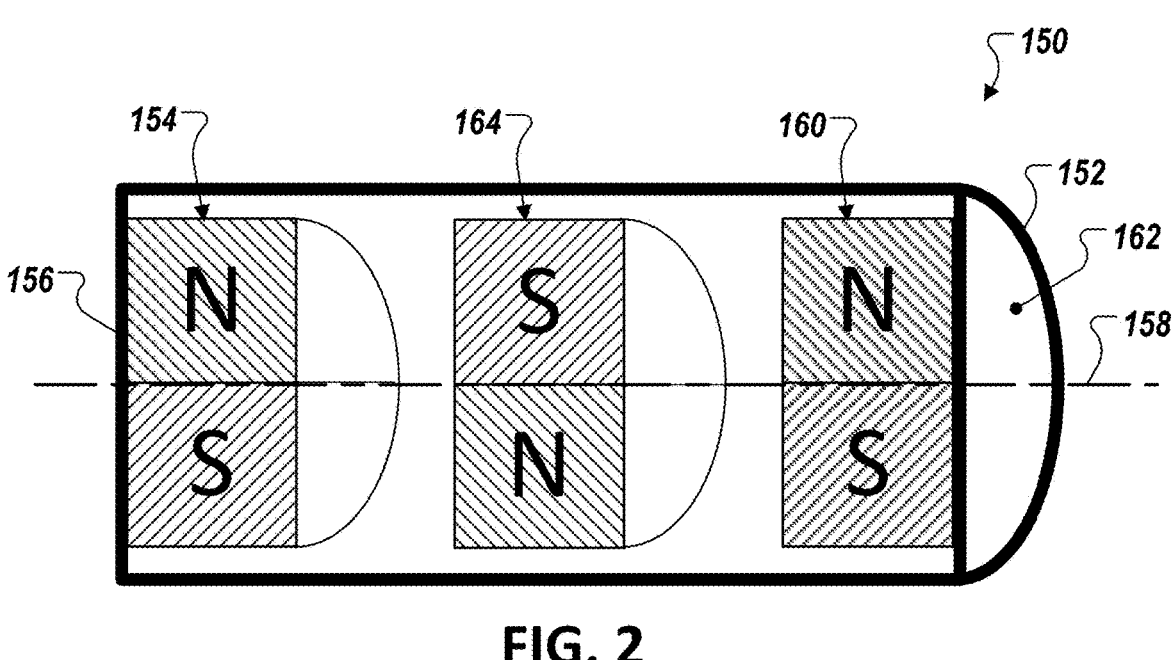
FIG. 2 is a cross-section of the magneto-mechanical capsule of FIG. 1.

FIG. 2 is a cross-section of one example of a magneto-mechanical capsule 150. The magneto-mechanical capsule 150 includes a body 152. In some implementations, the body 152 is or includes a hard (e.g., rigid) outer shell. In some implementations, the body 152 is formed by two halves that are joined together after assembly to close or seal the magneto-mechanical capsule 150. This seal prevents or limits bodily fluids from penetrating the interior of the magneto-mechanical capsule 150. While the body 152 is represented as a cylinder with flat ends in FIG. 2, the body 152 can be employ various types of geometries. For example, the body 152 can include rounded edges and resemble a "pill" shape as shown in FIG. 1. In some examples, the body 152 can be cube-shaped. Various sizes and geometries provide various different design tradeoffs (e.g., maximize magnetic dipole moment to improve signal quality vs. minimize diameter to fit within the anatomy of the patient 104, etc.). In some implementations, the body 152 is diamond-shaped, square-shaped, oval-shaped, etc.

The magneto-mechanical capsule 150 includes a first magnet 154 attached to a first end 156 of the body 152. In some implementations, one or more adhesives (e.g., UV curable glue) are used to attach the first magnet 154 to the first end 156 of the body 152. In other examples, mechanical techniques are used to attach the first magnet 154 to the first end 156 of the body 152 (e.g., straps, Velcro®, etc.). The first magnet 154 includes north and south poles which are represented with an "N" and an "S" in the figures, respectively. The north and south poles produce a permanent magnetic dipole moment. In this example, the first magnet 154 is disc-shaped and is concentrically disposed along a longitudinal axis 158 of the body 152. The north pole is arranged on a first side of the longitudinal axis 158 and the south pole is arranged on a second side of the longitudinal axis 158. In other words, the first magnet 154 is arranged such that the north and south poles span a transverse direction of the longitudinal axis 158.

The magneto-mechanical capsule 150 includes a second magnet 160 attached to an opposite second end 162 of the body 152 (e.g., by one or more adhesives, using mechanical techniques, etc.). The second magnet 160 is identical to the first magnet 154 and is arranged the same way as the first magnet 154 (e.g., concentrically disposed along the longitudinal axis 158 and has north and south poles that span a transverse direction of the longitudinal axis 158). Furthermore, the orientation of the north and south poles of the second magnet 160 are in the same direction as the north and south poles of the first magnet 154 and thus produce the same magnetic dipole moment as the first magnet 154.

The magneto-mechanical capsule 150 includes a third magnet 164 disposed between the first magnet 154 and the second magnet 160. In some implementations, the third magnet 164 is disposed equidistantly between the first magnet 154 and the second magnet 160. The third magnet 164 has north and south poles that are arranged in an opposite direction to the north and south poles of the first magnet 154 and the second magnet 160 such that the magnetic dipole moment produced by the third magnet 164 is opposite to the magnetic dipole moments produced by the first and second magnets 154, 160. This arrangement of north and south poles allows the third magnet 164 to be in mechanical equilibrium within the body 152 while also being spaced apart from the first magnet 154 and the second magnet 160.

However, while the third magnet 164 is in mechanical equilibrium, the third magnet 164 can oscillate out of mechanical equilibrium. Generally, the presence of the first and second magnets 154, 160 provide a restoring force or torque on the third magnet 164 to assist the third magnet 164 back to its mechanical equilibrium position. In some implementations, the first magnet, the second magnet, and the third magnet are disc-shaped or cylindrical, however other shapes are possible. In some implementations, the first magnet, the second magnet, and/or the third magnet diamond-shaped, square-shaped, oval-shaped, etc.

Figure 3:
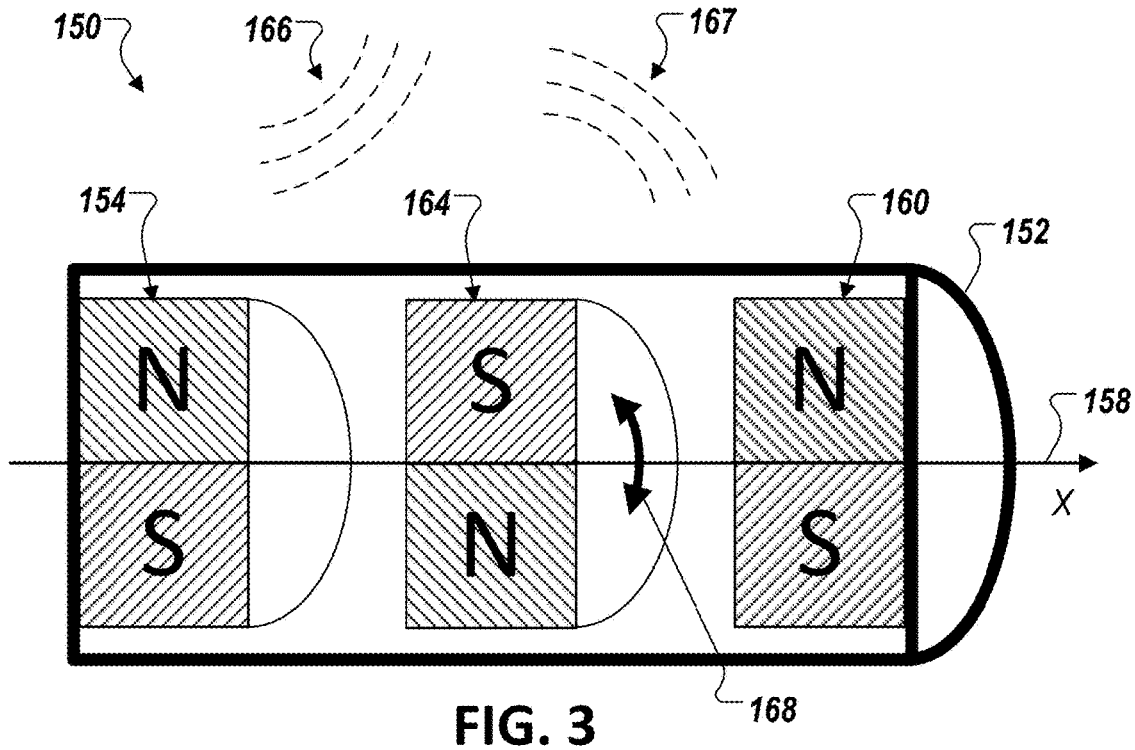
FIG. 3 shows a magnet of the magneto-mechanical capsule of FIG. 1 oscillating in the presence of an external magnetic field.

FIG. 3 shows the magneto-mechanical capsule 150 being exposed to the external magnetic field 166. The external magnetic field 166 excites one or more resonances of the rotational degree of freedom of the third magnet 164. Preferably, these resonances have low frequency (e.g., less than 3 kHz, approximately 2 kHz, etc.) and are different than resonances about the other axes (both rotational and translational). This means that, when the third magnet 164 is exposed to an external magnetic field 166 having a particular frequency range (e.g., 1.5 kHz-3 kHz), the third magnet 164 begins to oscillate about the longitudinal axis 158 while remaining relatively stationary otherwise. For example, the presence of the external magnetic field 166 causes the third magnet 164 to oscillate 168 in a rotational direction (e.g., rotationally oscillate) about the longitudinal axis 158 (or axis "X") at one or more frequencies of its one or more resonances while minimally moving in the other directions. The rotational oscillation 168 of the third magnet 164 produces an oscillating magnetic dipole in space-represented by magnetic field 167. The external magnetic field 167 is measurable by the transducers 122 (or by another sensor of the system). In some examples, the rotational oscillation 168 is 20 degrees or less (e.g., less than 10 degrees, less than 5 degrees, less than 2 degrees, etc.)

Figure 4:
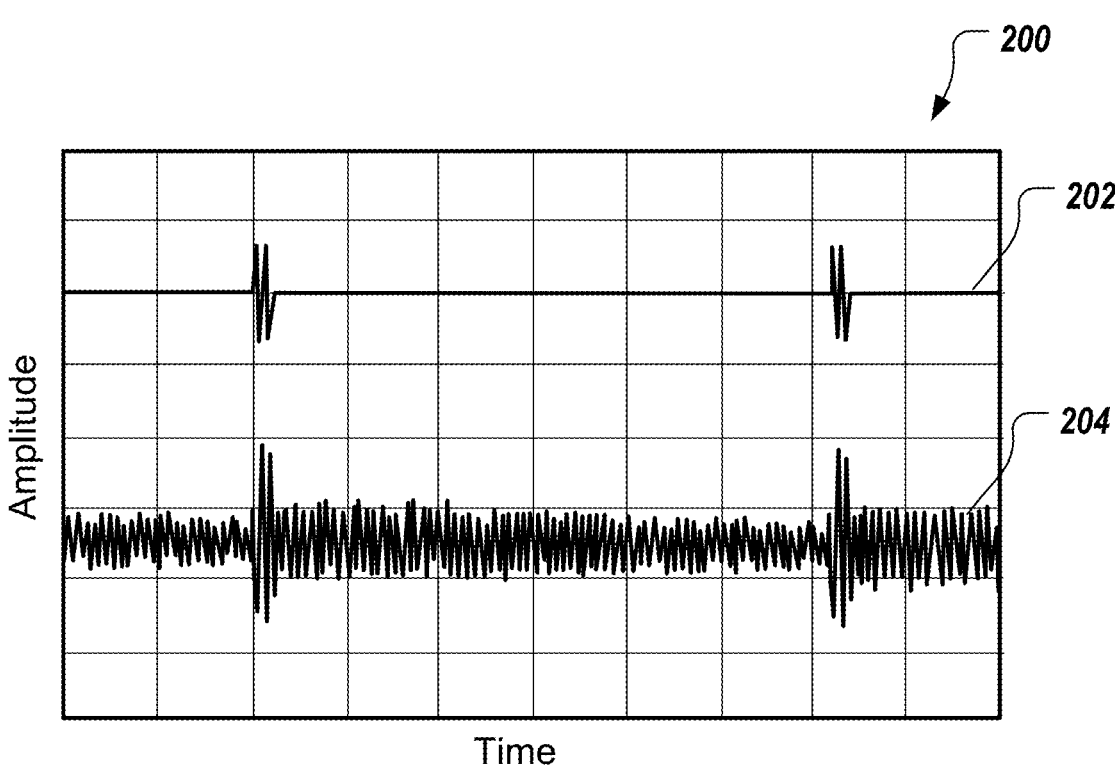
FIG. 4 is a time-domain plot illustrating voltages of an external magnetic field.

FIG. 4 is a time-domain plot 200 illustrating voltages of the external magnetic field 166. The one or more processors of the computer system 108 generate transmit pulses (e.g., upper trace 202 in FIG. 5) that are amplified using an audio amplifier and then sent to transmit coils of the transducers 122. FIG. 4 shows, besides the transmit pulses 202, the induced voltage 204 in a receive coil of the transducers 122. The spacing of the excitation pulses 204 can be continuously adjusted by the one or more processors of the computer system 108. Once the transducers 122 measure the time-domain induced voltage 204 representing the magnetic field 167, the computer system 108 receives the induced voltage 204 and performs a Fast Fourier Transform (FFT) on the time-domain signal induced voltage 204 to produce a frequency-domain signal representing the magnetic field 167.

Figure 5:
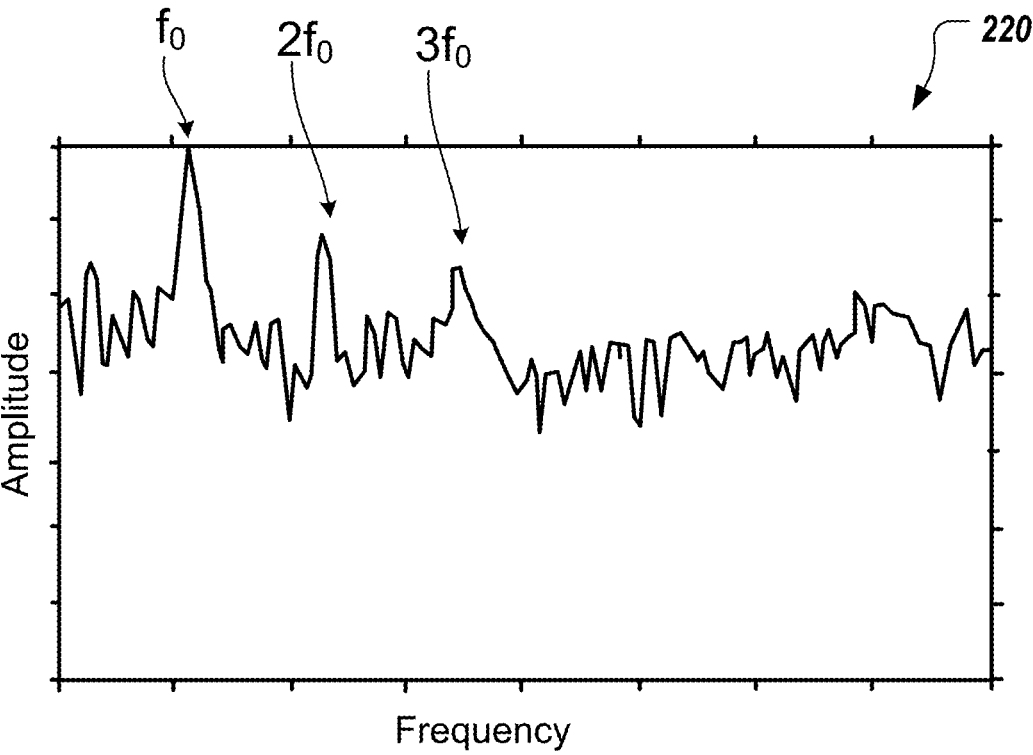
FIG. 5 is a frequency-domain plot illustrating resonances caused by example magneto-mechanical capsules.

FIG. 5 is a frequency-domain plot 220 illustrating one or more resonances caused by the magneto-mechanical capsules described herein. The one or more resonance frequencies of the oscillating magnet are detectable by the computer system 108. Specifically, the fundamental frequency of oscillation of the third magnet 164 is represented as $f_0$, with second and higher harmonics represented as $2f_0$, $3f_0$, etc. In some implementations, the computer system 108 determines the magnitude of the peaks in the time-domain or frequency-domain and uses these peaks to determine the position and/or orientation of the magneto-mechanical capsule 150.

In some implementations, the computer system 108 matches the different amplitudes of the receive signals together with the known coil element sensitivities to a dipole model to determine the position and orientation parameters of the magneto-mechanical capsule 150. One approach to determine the position and/or orientation of the magneto-mechanical capsule 150 within the patient 104 is to perform a position determination based on coil sensitivity for each coil in a coil array of the transducers 122. This approach is based on the fact that each coil in a coil array has a different spatial sensitivity profile $B_{s,r}(r)$ based on its position and orientation.

Another approach is based on gradient field encoding. Gradient field encoding approach is based on the fact that the frequencies of the magneto-mechanical capsule 150 can be manipulated to give independent position information. For this purpose, a non-uniform magnetic field, ideally having a constant field gradient over the workspace, may be generated, e.g., by applying low frequency currents to selected ones of the coils in the coil array. Such a non-uniform field could for example be achieved by providing independent control of the coils of the transducers 122. This additional field changes a restoring field acting $B_{rest}$ on a magnetic object of the sensing unit and, thus, changes the frequency of the oscillation. Due to the non-uniform nature of the magnetic or electromagnetic field, this frequency change will depend on the position and orientation of the magneto-mechanical capsule 150.

If the external magnetic field 166 is aligned parallel to the magnetic dipole orientation of the magneto-mechanical capsule 150, no excitation occurs, and the sensed signal by the transducer 122 is negligible. For orthogonal alignment of the external magnetic field 166 and the magnetic dipole orientation, the highest oscillation amplitude is achieved. Knowledge that the dynamic response at even harmonics is oriented orthogonally to that of odd harmonics can be used to determine an orientation angle of the magneto-mechanical capsule 150. It is possible to obtain the position and/or orientation of the magneto-mechanical capsule 150 and hence, of the catheter 118, by either sensitivity encoding or by gradient encoding. In some implementations, a combination of both may be employed.

FIG. 6 is a flowchart of a method 250 that uses the magneto-mechanical capsule 150. In some implementations, one or more components of the computer device 400 or the example mobile computer device 450 described with reference to FIG. 16 perform one or more steps of the method 250.

At step 252, the method 250 includes transmitting, by a transducer, a first magnetic field. For example, one or more of the transducers 122 transmit the magnetic field 167.

At step 254, the method 250 includes rotationally oscillating a third magnet of the magneto-mechanical capsule to produce an oscillating second magnetic field, the rotational oscillation being caused by an excitation of one or more resonances of the third magnet by the presence of the first magnetic field, the free magnet being spaced apart from and between a first magnet of the magneto-mechanical capsule and a second magnet of the magneto-mechanical capsule. For example, the external magnetic field 166 causes a rotational oscillation 168 of the third magnet 164 of the magneto-mechanical capsule 150 about a longitudinal axis 158 of the magneto-mechanical capsule 150 to produce the oscillating second magnetic field 167. The third magnet 164 is spaced apart from and between the first magnet 164 and the second magnet 160.

At step 256, the method 250 includes receiving, at the transducer, the oscillating second magnetic field. For example, the transducers 122 receive the magnetic field 167.

At step 258, the method 250 includes determining the position or orientation of the magneto-mechanical capsule based on the oscillating second magnetic field. For example, the computer system 108 receives one or more signals from the transducer 122 representing the magnetic field 167 and determines a position or orientation of the magneto-mechanical capsule 150 based on the signals.

In some implementations, the method 250 is performed while the magneto-mechanical capsule 150 is inserted into a patient (e.g., patient 104) such that the determined position of the magneto-mechanical capsule 150 represents a position or orientation of the magneto-mechanical capsule 150 within the patient 104. In some implementations, the computer system 108 presents the determined location within an anatomy of the patient 104 on a display 110 of the computer system 108.

In some implementations, the method 250 includes stopping the transmitting of the first magnetic field after rotationally oscillating the third magnet of the magneto-mechanical capsule and before receiving the oscillating second magnetic field. For example, the transducers 122 are switched from a transmit mode to a receive mode to receive the magnetic field 167.

In some implementations, the computer system 108 determines all three cartesian coordinate positions and all three rotations (e.g., pitch, roll, and yaw) of the magneto-mechanical capsule 150.

Figure 7:
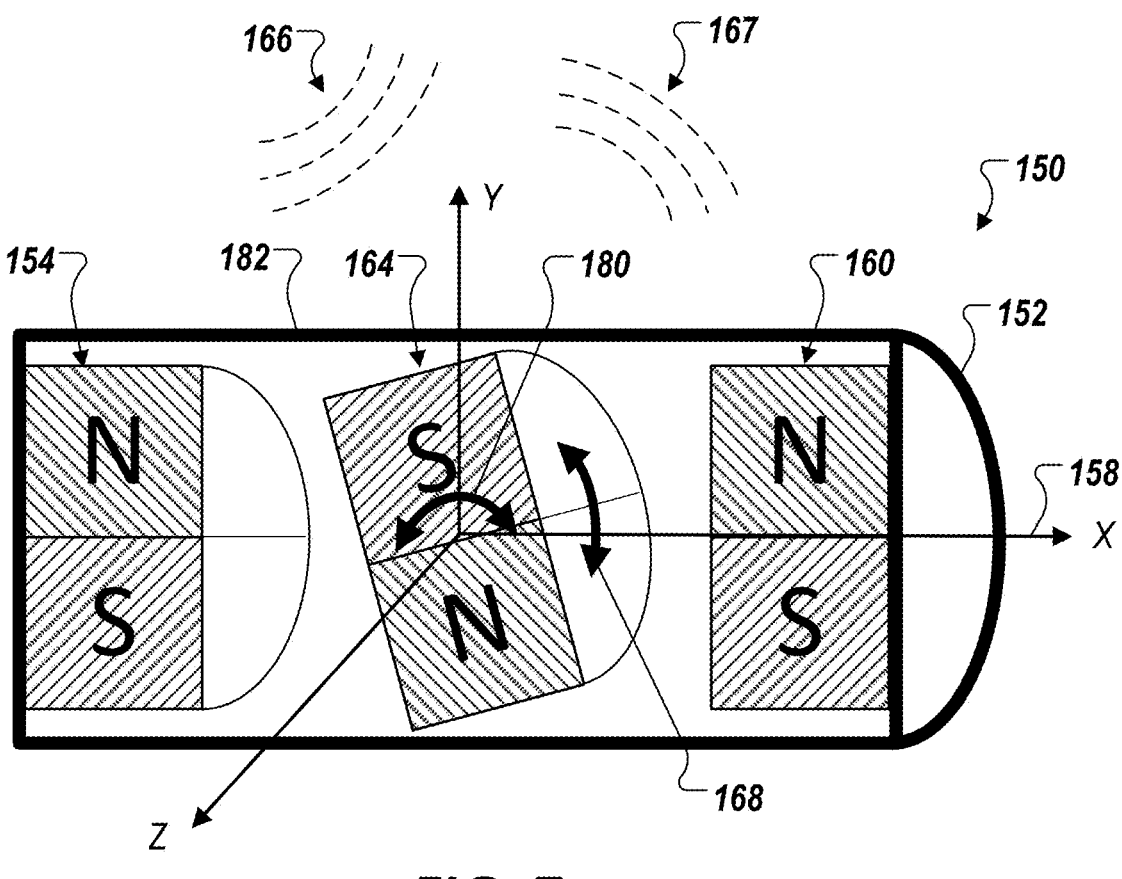
FIG. 7 shows a magnet of the magneto-mechanical capsule of FIG. 1 oscillating and wobbling in the presence of an external magnetic field.

FIG. 7 illustrates instability that can occur in which the third magnet 164 of the magneto-mechanical capsule 150 wobbles about an axis perpendicular to the longitudinal axis 158 (e.g., axis "Z") of the magneto-mechanical capsule 150 either during oscillation about the longitudinal axis 158 or prior to oscillation about the longitudinal axis 158. While the wobbling is illustrated to be about axis "Z," in some cases the wobbling is about axis "Y," or a combination thereof. The wobbling is represented by arrow 180 and is generally undesirable because the wobbling can cause the third magnet 164 to contact the sidewall 182 of the body 152 and/or the first and second magnets 154, 160. The wobbling may also cause other resonances to appear in the frequency-domain plot (e.g., as shown in FIG. 5) which can be accounted for by the computer system 108 to avoid erroneous position and orientation determinations.

Furthermore, contact between the third magnet 164 and the sidewall 182 of the body 152 and/or the first and second magnets 154, 160 can severely limit the ability of the third magnet 164 to oscillate (e.g., by reducing the amplitude of the vibration in half or worse). Additionally, the friction between these components can negatively affect the rotational oscillation 168. Decreased rotational oscillation 168 can cause a measurable decrease in the strength of the magnetic field 167—which means that the transducers 122 may be unable to sense the magnetic field 167 and the computer system 108 may be unable to accurately determine the position or orientation of the magneto-mechanical capsule 150.

Thus, it is desirable to minimize or reduce impacts and friction of the third magnet 164 as well as preferably limiting the ability of the third magnet 164 to move or rotate in any degree of freedom other than the rotational direction 168 about the longitudinal axis 158.

In some implementations, rotational friction is reduced by extracting air from the interior of the magneto-mechanical capsule 150. For example, a vacuum (not shown) can be used to extract air from the interior of the magneto-mechanical capsule 150 during assembly. Reducing the air resistance within the body 152 decreases the rotational friction of the third magnet 164 which in turn allows the third magnet 164 to oscillate faster to produce a stronger magnetic field 167.

Figure 8:
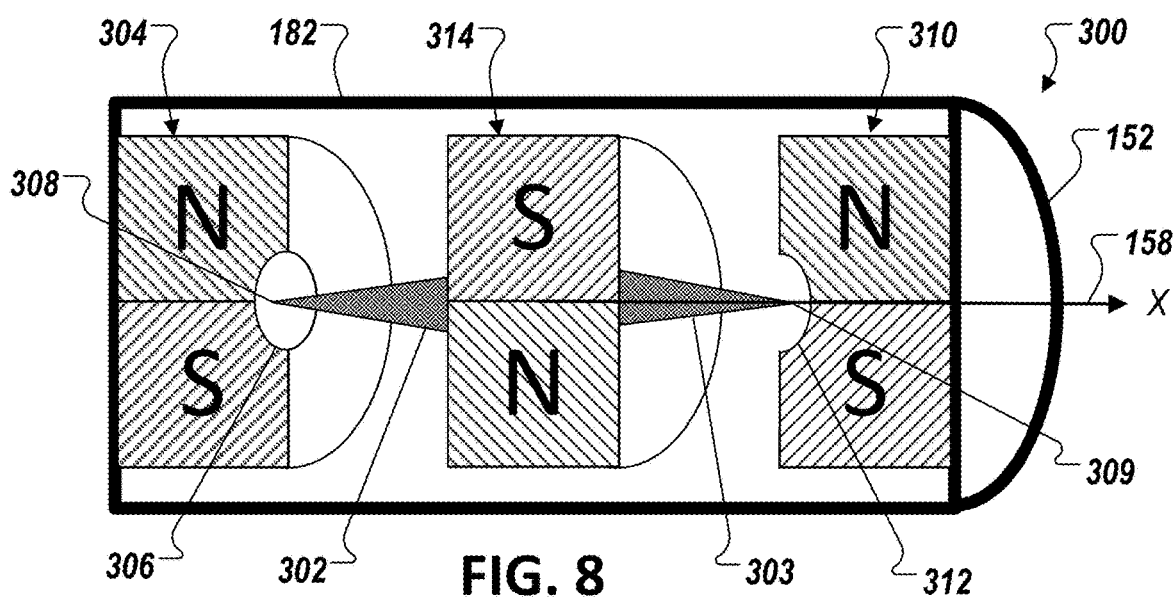
FIG. 8 shows a magneto-mechanical capsule with pin stabilizers.

FIG. 8 shows a magneto-mechanical capsule 300 with one or more stabilizers 302, 303 implemented as pins 302, 303. The stabilizing pins 302, 303 limit a rotation of the third magnet 314 about an axis perpendicular to the longitudinal axis 158 (e.g., wobbling). The pins 302, 303 include endings 308, 309 that contact a sidewall of cavities 306, 312 of the first and second magnets 304, 310, respectively, to limit the wobbling. Thus, while a small amount of contact and wobbling is permitted with the design represented in FIG. 8, this design provides a good tradeoff between permitted wobbling and contact.

The magneto-mechanical capsule 300 is similar to the magneto-mechanical capsule 150 except for the following differences. In addition, like elements with the magneto-mechanical capsule 150 are indicated with the same Arabic numerals. The magneto-mechanical capsule 300 includes a third magnet 314 with a first pin 302 extending in a first longitudinal direction (e.g., to the left as shown in FIG. 8) from the third magnet 314 and having an end 308 that is disposed within a cavity 306 of the first magnet 304. The third magnet 314 also has a second pin 303 extending in a second opposite longitudinal direction (e.g., to the right as shown in FIG. 8) from the third magnet 314 and having an end 309 that is disposed within a cavity 312 of the second magnet 310. While the ends 308, 309 are depicted as pointed ends, in some implementations, the ends 308, 309 are rounded or blunt.

Furthermore, while each side of the third magnet 314 is depicted as including a single stabilizing pin 302, 303, in some implementations, each side of the third magnet 314 includes multiple pins (e.g., two or more pins, or a pattern of pins). Similarly, in some implementations, two or more pins are used on the surface of the third magnet 314 that employs stabilizing pin 303. While in some implementations the pin layout on each side of the third magnet 314 is identical (e.g., two or three pins on each surface), different pin layouts could be used on the two surfaces of the third magnet 314. Furthermore, some implementations include stabilizing pins extending inward from the first and second magnets 304, 310 instead of outward from the third magnet 314.

Additionally, or alternatively, some implementations do not include cavities 306, 312. In examples where cavities 306, 312 are omitted, the one or more stabilizing pins 302, 303 can contact one or more surfaces of the first and second magnets 304, 310 to limit wobbling of the third magnet 314. Hence, the cavity can be very small or not present at all and the one or more stabilizing pins 302, 303 can be used limit any movement of the third magnet 314 in the longitudinal direction. The oscillation of the third magnet 164 around longitudinal axis can be limited by a bushing (e.g., bushing 352) or by the sidewall 182 of the surrounding cylinder defining the body 152.

Figure 9:
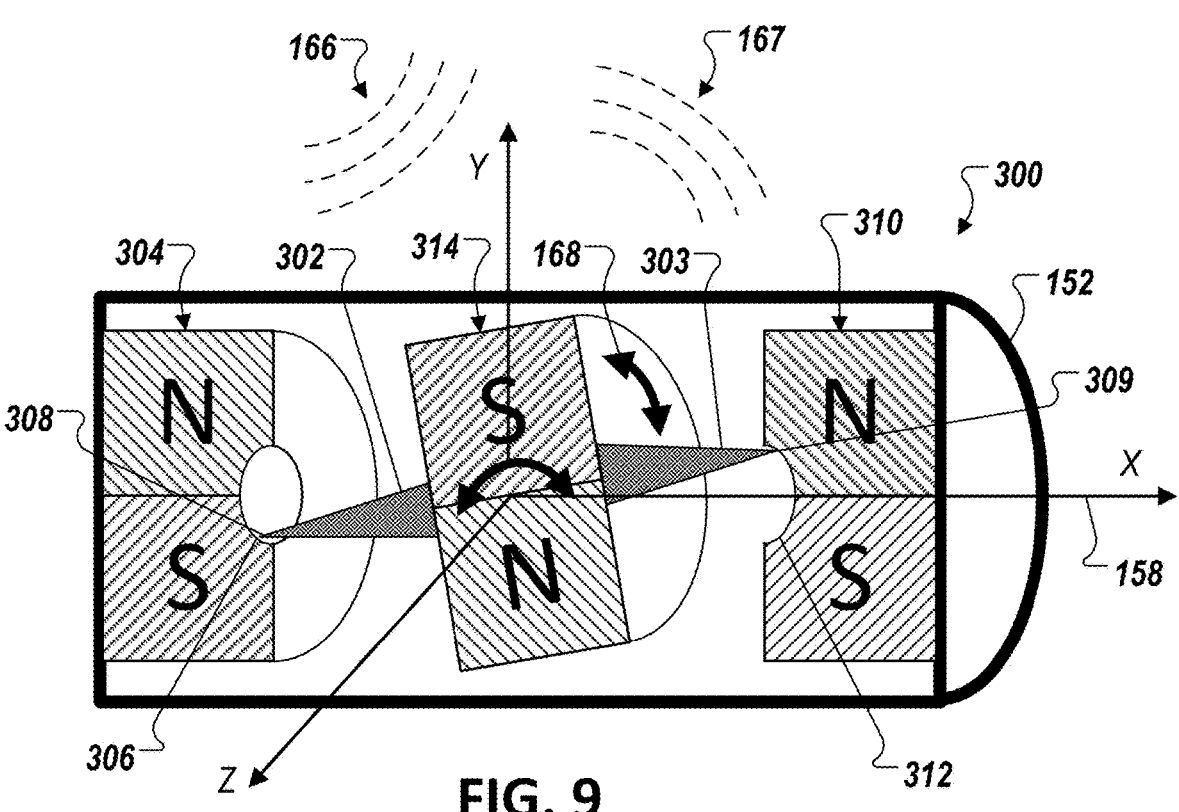
FIG. 9 shows the limited wobbling of the magneto-mechanical capsule of FIG. 8 due to the pin stabilizers.

FIG. 9 shows the limited wobbling of the magneto-mechanical capsule 300. As the third magnet 314 wobbles about the Z axis, the ends 308, 309 contact a sidewall of the cavities 306, 312 of the first and second magnets 304, 310, respectively, to limit the wobbling. Specifically, the respective ends 308, 309 of the first and second pins 302, 303 are configured to move within the respective cavities 306, 312 of the first and second magnets 304, 310 and contact the sidewall of the cavities 306, 312 in response to the external magnetic field 166. Contact between the ends 308, 309 and the sidewall of the cavities 306, 312 of the first and second magnets 304, 310 limits a rotation of the third magnet 314 about an axis perpendicular to the longitudinal axis 158 (e.g., about the "Z" axis, the "Y" axis, or a combination).

In some implementations, the cavities 306, 312 are sized to limit the wobbling to less than 20 degrees relative to the longitudinal axis (e.g., less than 10 degrees, less than 5 degrees, less than 2 degrees, etc.). Additionally, while the stabilizer is implemented as two pins 302, 303, some implementations include one pin arranged on a single side of the third magnet 314. (See, e.g., the implementation described with reference to FIG. 13). In some implementations, the cavities 306, 312 are formed in the first and second magnets 304, 310 by drilling a hole in the magnets that is concentric with the longitudinal axis 158.

Figure 10:
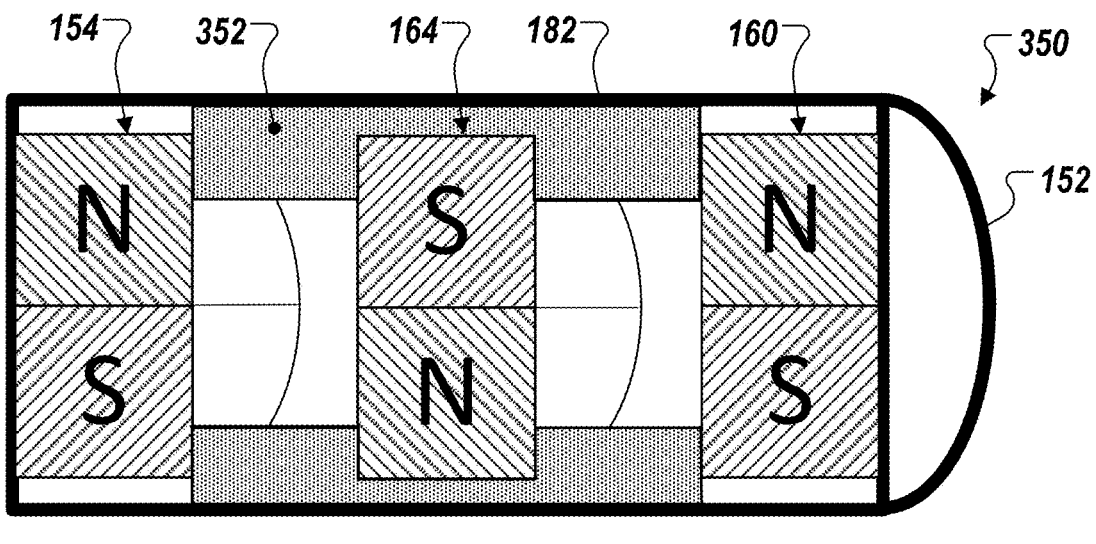
FIG. 10 shows a magneto-mechanical capsule with a sleeve stabilizer.

FIG. 10 shows a magneto-mechanical capsule 350 with a stabilizer 352 implemented as a bushing 352. The magneto-mechanical capsule 350 includes the same, or substantially similar, magnets as the magneto-mechanical capsule 150. However, the bushing 352 (e.g., a sleeve bushing) is disposed circumferentially around the third magnet 164. In some implementations, the bushing 352 is in slidable contact with at least one of the first magnet 154, the second magnet 160, or the sidewall 182 of the body 152. The bushing 352 limits the rotation of the third magnet 164 about an axis perpendicular to the longitudinal axis 158 by limiting an axial movement of the third magnet 164 within the body 152. For example, rotation about the Y and Z axes is limited.

Figure 11:
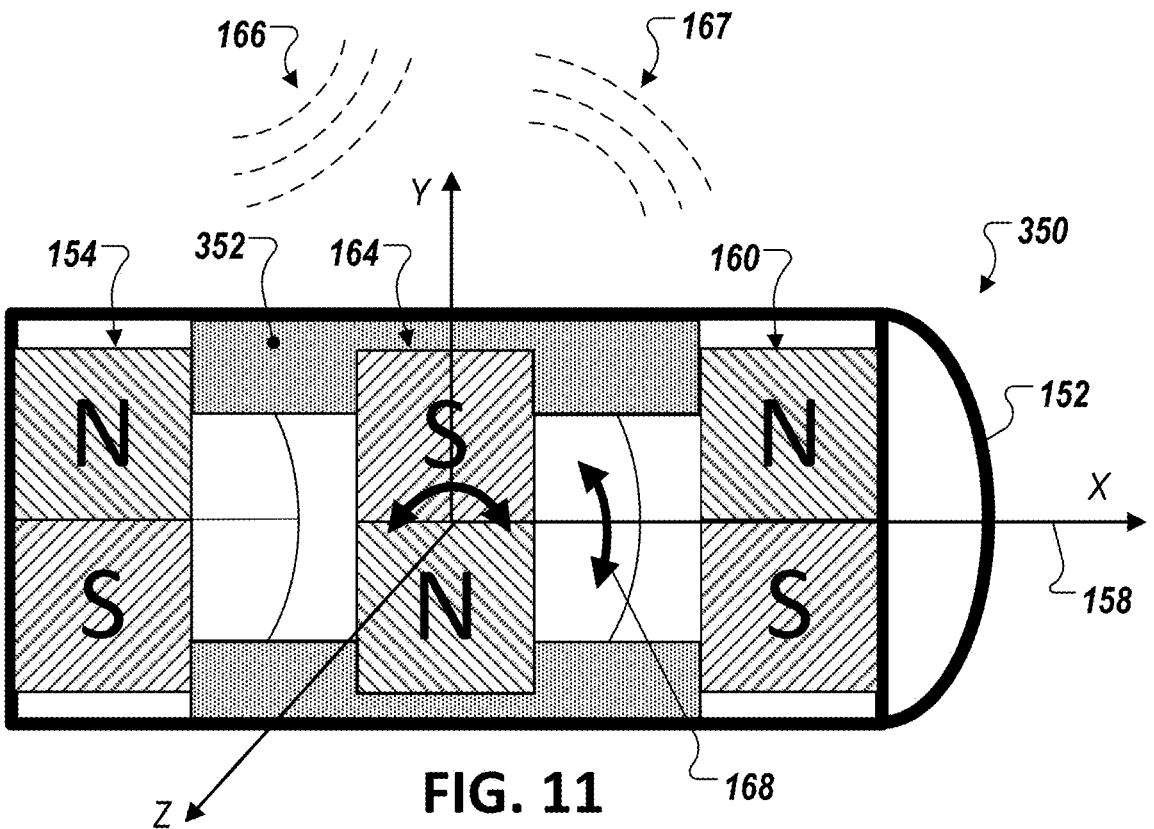
FIG. 11 shows the limited wobbling of the magneto-mechanical capsule of FIG. 10 due to the sleeve stabilizer.

FIG. 11 shows the limited wobbling of the magneto-mechanical capsule 350 due to the bushing 352. As the third magnet 164 starts to wobble 180 about the Y and/or Z axes, the third magnet 164 contacts the bushing 352 and slides against the bushing 352. The sliding contact limits the wobbling. The bushing 352 is formed of a low friction material (e.g., polytetrafluoroethylene (PTFE), polyimide, Polyetheretherketone (PEEK), Polyphenylene sulfide (PPS), Nylon, Acetal, or Polyester).

In some implementations, one or more surfaces of the bushing 352 is coated with (or injected with) one or more fluids or other low friction materials (e.g., a coating on the outer surface of the third magnet 164 or the inner surface of the bushing 365 in contact with the third magnet 164). In some cases, this coating reduces friction between the third magnet 164 and the bushing 352.

In some implementations, the bushing 352 is a cylinder that extends 360 degrees around the third magnet 164. However, there might be friction between the contact area around the perimeter of the disc-shaped third magnet 164 and the inside surface of the bushing 352. To reduce this friction, the surface of can be modified to reduce the contact area of the third magnet 164 to the surface of the bushing 352. For example, the third magnet 164 can be shaped like a cog wheel or gear to reduce the surface area on the outside surface of the disc-shaped third magnet 164 as described with reference to FIGS. 12 and 13.

Figure 12:
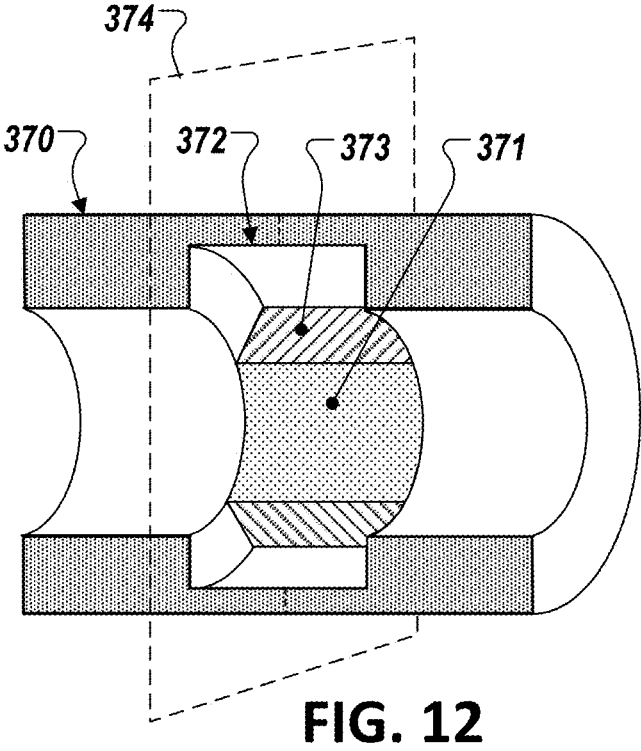
FIG. 12 shows a first cross-section of an example cogwheel stabilizer.
Figure 13:
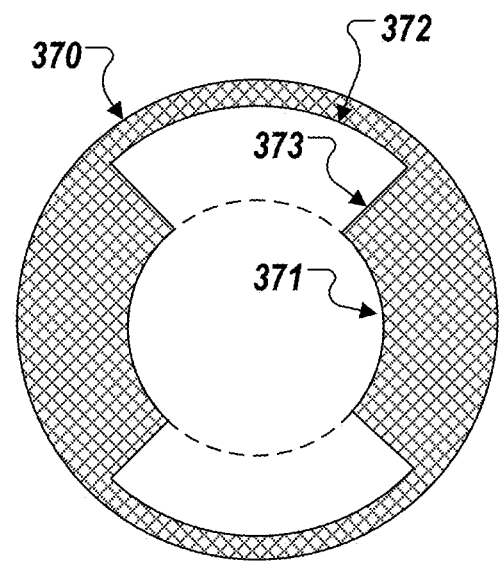
FIG. 13 shows a second cross-section of the example cogwheel stabilizer of FIG. 12.

FIG. 12 shows a first cross-section of an example stabilizer 370 that is implemented as a cogwheel stabilizer 370. FIG. 13 shows a second cross-section of the cogwheel stabilizer 370 with respect to plane 374 perpendicular to the cross section of FIG. 12. The cogwheel stabilizer 370 is similar to the bushing 352 except that portions 372 have been removed to reduce friction between the third magnet 164 and the sidewall 182, the first magnet 154, and/or the second magnet 160. For example, the cogwheel stabilizer 370 includes one or more inward protrusions 371 with one or more cavities 372 circumferentially disposed the one or more inward protrusions 371. The one or more cavities 372 reduce the amount of contact between the third magnet 164 and the sidewall 182, the first magnet 154, and/or the second magnet 160. In some examples, the cogwheel stabilizer 370 resembles a cogwheel or gear with "teeth"—e.g., the one or more inward protrusions 371 may be considered "teeth." In some examples, the one or more inward protrusions 371 include one or more surfaces 373 at least partially defining the one or more cavities 372.

While the cogwheel stabilizer 370 includes two inward protrusions 371, other implementations include more than two one or more inward protrusions 371 (e.g., 3-10). Additionally or alternatively, the first and second magnets 154, 160 can also be shaped like a cog wheel or gear to reduce the friction between the third magnet 164 and the sidewall 182, the first magnet 154, and/or the second magnet 160.

In some implementations, the bushing 352 is formed by two halves that slide together around the third magnet 164 along the longitudinal direction to encapsulate the third magnet 164. In some examples, a two-part bushing 352 improves assembly of the magneto-mechanical capsule 350. In some implementations, the "seam" is oriented along the Y axis such that each half has substantially the same size and shape. In some implementations, the two halves join together using one or more mechanical connectors (e.g., snap features or pins).

Figure 14:
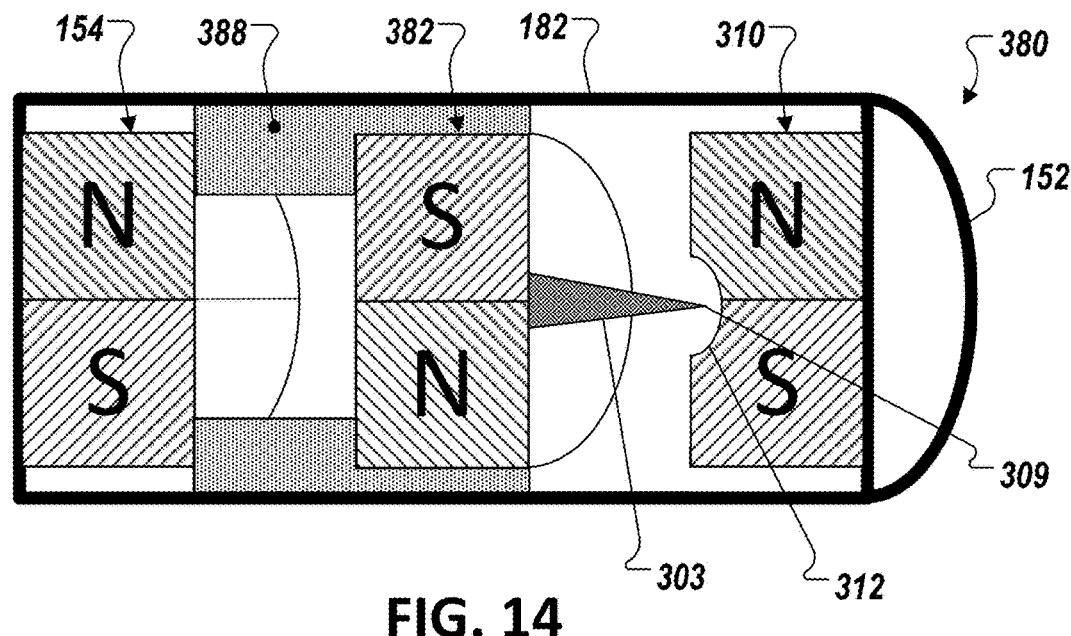
FIG. 14 shows a magneto-mechanical capsule with a cup stabilizer and a pin stabilizer.

FIG. 14 shows a magneto-mechanical capsule 380 with a stabilizer 384, 388. The stabilizer is implemented as a cup stabilizer 388 and a pin stabilizer 384. In some implementations, the cup stabilizer 388 is the bushing 352 with a portion removed. Specifically, in this example, the cup stabilizer 388 forms the left-side portion of the bushing 352 and the portion of the bushing 352 located between the sidewall 182 and the third magnet 382. However, other shapes and sized can be implemented (e.g., the portion of the bushing 352 located between the sidewall 182 and the third magnet 382 can be removed, and/or the portion to the left-side of the third magnet 382 can be removed). The third magnet 382 is generally the same as the third magnet 164 except that it includes the stabilizer pin 303. As described with reference to FIGS. 8 and 9, the stabilizer pin 303 has an end 309 that contacts a sidewall of the cavity 312 of the second magnet 310 to limit wobbling of the third magnet 382.

Figure 15:
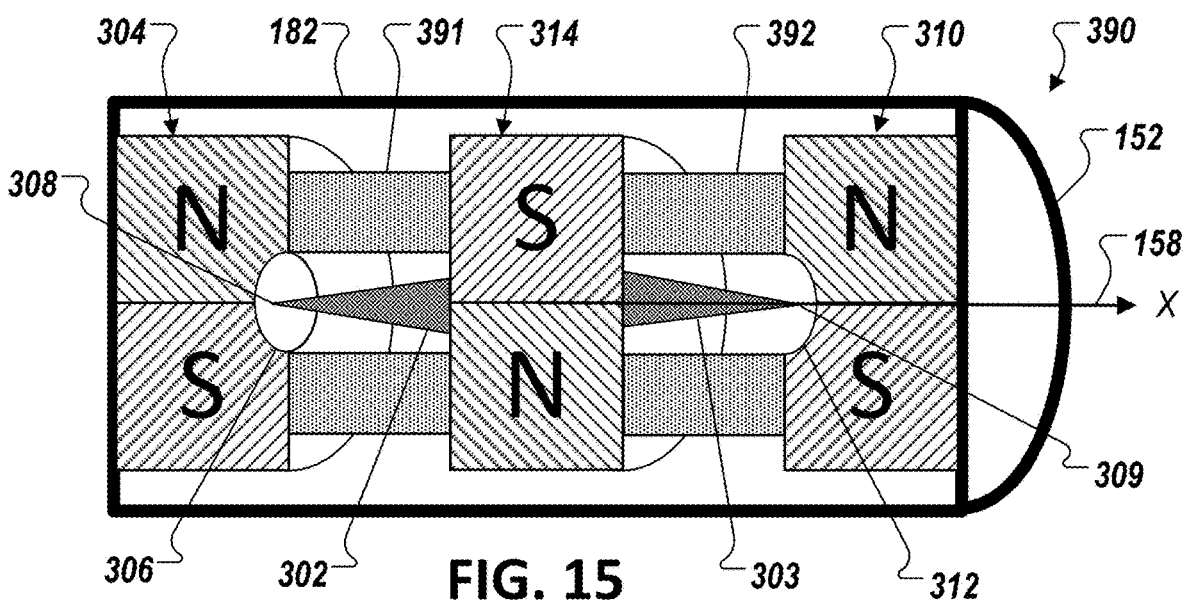
FIG. 15 shows a bushing stabilizer surrounding pin stabilizers.

FIG. 15 shows two stabilizers 391, 392 implemented as bushings 391, 392 surrounding respective pin stabilizers 302, 303. Bushing 391 is disposed (i) around the stabilizing pin 302 and (ii) between the first magnet 304 and the third magnet 314. Bushing 392 is disposed (i) around the stabilizing pin 303 and (ii) between the second magnet 310 and the third magnet 314. In some implementations, the bushings 391, 392 are sleeves that span an entire circumference (e.g., are complete 360-degree annular rings). The presence of the bushings 391, 392 can further limit wobbling of the third magnet 314 as well as limit axial movement of the third magnet 314 relative to the first and second magnets 304, 310.

In some implementations, the magneto-mechanical capsules include one or more stabilizers (e.g., one or more stabilizer pins 302, 303, one or more stabilizing sleeves 352, 391, 392, one or more stabilizing cups 388, one or more stabilizing cog-wheel sleeves 370, etc., or a combination thereof). In some implementations, the one or more stabilizers reduce rotational friction between the third magnet 164, 314, 382 and the first and second magnets 154, 310, and the sidewall 182 of the body 152.

While the magneto-mechanical capsule examples depicted herein include three magnets, some implementations include more than three magnets (e.g., 4-10 magnets). For example, some magneto-mechanical capsules include five magnets arranged in a stack with alternating polarity such that the magnets are spaced apart and exist in a mechanical stable state prior to being exposed to an external magnetic field. In addition, each magnet can have a different mass with different resonance frequencies, thereby providing multiple different frequencies that can be detected by the transducers 122.

While the medical environments depicted herein use a single magneto-mechanical capsules, some environments use multiple magneto-mechanical capsules and are configured to determine the position and orientation of multiple magneto-mechanical capsules within the anatomy of the patient based on differences in resonance frequencies of the oscillating magnets.

In some implementations, one or more magneto-mechanical capsule 150 are used throughout the medical environment to track the location of more or more medical instruments (e.g., guide wires, sensor, patient body parts, etc.).

While the transducers 122 are described as being configured to both transmit the magnetic field 166 and receive the magnet field 167, in some implementations separate devices perform these functions. For example, a transmitter transmits the magnetic field 166 and a separate receiver receives the magnetic field 167.

In some examples, the magnetic field 166 is shut off while the magnetic field 167 is sensed. In other examples, the magnetic field 166 is left on while the magnetic field 167 is sensed.

While the body 152 of the magneto-mechanical capsule 150 is rigid in the examples described herein, in some implementations, the body 152 is flexible. For example, implementing the body 152 as a flexible material allows the magneto-mechanical capsule 150 to be used as a pressure or temperature sensor. For example, a plastic body 152 may deform under pressure and temperature. This deformation will change the relative positioning of the magnets within the magneto-mechanical capsule 150 which in turn changes the strength of the magnetic dipoles and hence the resonance frequencies of the acclimatable third magnet 154. The computer system 108 determines that the pressure or temperature has changed based on the change in frequencies.

Figure 16:
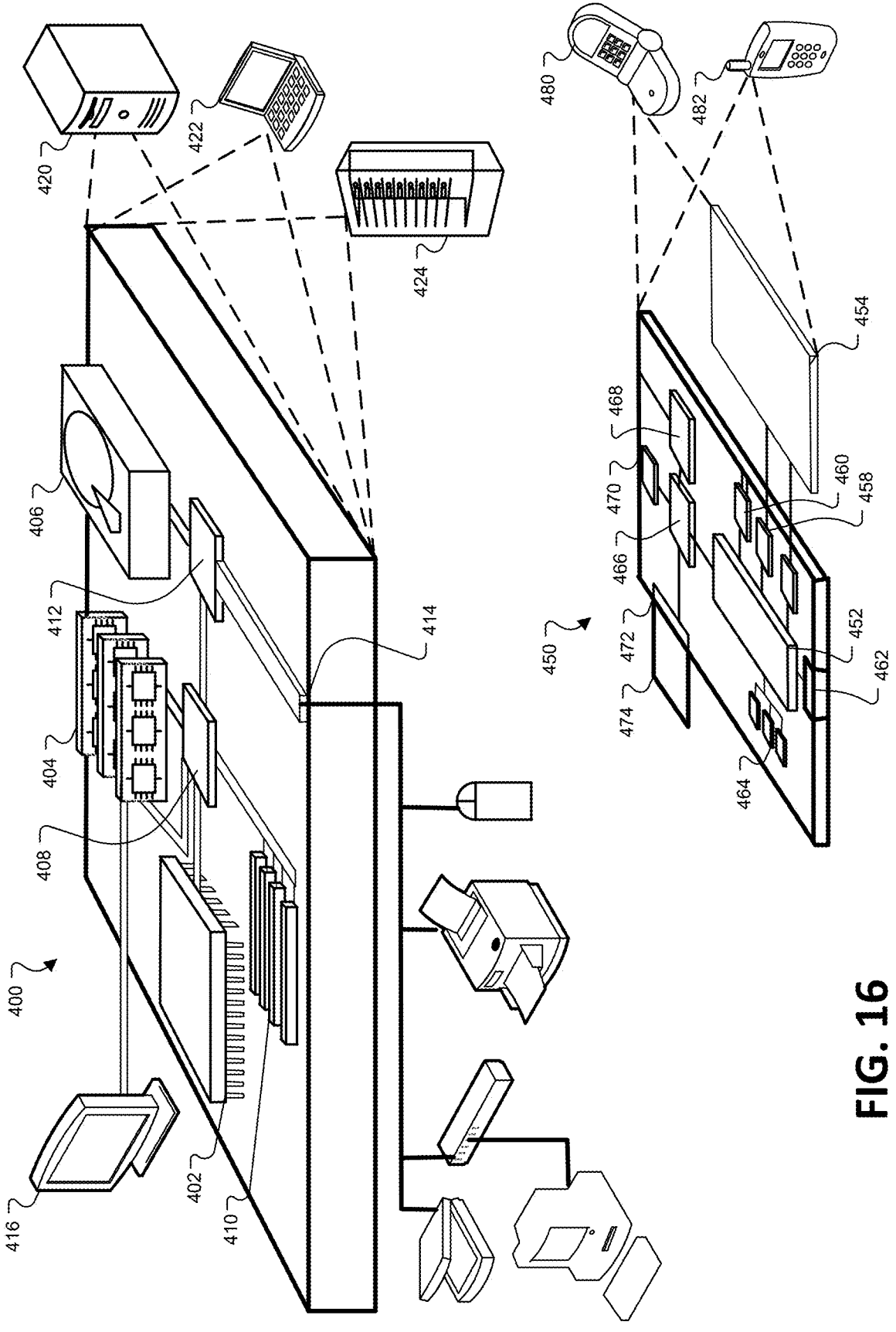
FIG. 16 shows an example computer device and an example mobile computing device for determining a position of magneto-mechanical capsules.

FIG. 16 shows an example computer device 400 and example mobile computer device 450 which can be used to implement the techniques described herein (e.g., method 250). In some implementations, the computer system 108 and/or the transducers 122 include one or more components of the example computer device 400 and example mobile computer device 450.

Computing device 400 is intended to represent various forms of digital computers, including, e.g., laptops, desktops, workstations, personal digital assistants, servers, blade servers, mainframes, and other appropriate computers. Computing device 450 is intended to represent various forms of mobile devices, including, e.g., personal digital assistants, tablet computing devices, cellular telephones, smartphones, and other similar computing devices. The components shown here, their connections and relationships, and their functions, are meant to be examples only, and are not meant to limit implementations of the techniques described and/or claimed in this document.

Computing device 400 includes processor 402, memory 404, storage device 406, high-speed interface 408 connecting to memory 404 and high-speed expansion ports 410, and low speed interface 412 connecting to low speed bus 414 and storage device 406. Each of components 402, 404, 406, 408, 410, and 412, are interconnected using various busses, and can be mounted on a common motherboard or in other manners as appropriate. Processor 402 can process instructions for execution within computing device 400, including instructions stored in memory 404 or on storage device 406 to display graphical data for a GUI on an external input/output device, including, e.g., display 416 coupled to high speed interface 408. In other implementations, multiple processors and/or multiple busses can be used, as appropriate, along with multiple memories and types of memory. Also, multiple computing devices 400 can be connected, with each device providing portions of the necessary operations (e.g., as a server bank, a group of blade servers, or a multi-processor system).

Memory 404 stores data within computing device 400. In one implementation, memory 404 is a volatile memory unit or units. In another implementation, memory 404 is a non-volatile memory unit or units. Memory 404 also can be another form of computer-readable medium (e.g., a magnetic or optical disk). Memory 404 may be non-transitory.

Storage device 406 is capable of providing mass storage for computing device 400. In one implementation, storage device 406 can be or contain a computer-readable medium (e.g., a floppy disk device, a hard disk device, an optical disk device, a tape device, a flash memory, or other similar solid state memory device, or an array of devices, such as devices in a storage area network or other configurations.) A computer program product can be tangibly embodied in a data carrier. The computer program product also can contain instructions that, when executed, perform one or more methods (e.g., those described above.) The data carrier is a computer- or machine-readable medium, (e.g., memory 404, storage device 406, memory on processor 402, and the like.)

High-speed controller 408 manages bandwidth-intensive operations for computing device 400, while low speed controller 412 manages lower bandwidth-intensive operations. Such allocation of functions is an example only. In one implementation, high-speed controller 408 is coupled to memory 404, display 416 (e.g., through a graphics processor or accelerator), and to high-speed expansion ports 410, which can accept various expansion cards (not shown). In the implementation, low-speed controller 412 is coupled to storage device 406 and low-speed expansion port 414. The low-speed expansion port, which can include various communication ports (e.g., USB, Bluetooth®, Ethernet, wireless Ethernet), can be coupled to one or more input/output devices, (e.g., a keyboard, a pointing device, a scanner, or a networking device including a switch or router, e.g., through a network adapter.)

Computing device 400 can be implemented in a number of different forms, as shown in the FIG. 16. For example, it can be implemented as standard server 420, or multiple times in a group of such servers. It also can be implemented as part of rack server system 424. In addition or as an alternative, it can be implemented in a personal computer (e.g., laptop computer 422.) In some examples, components from computing device 400 can be combined with other components in a mobile device (not shown), e.g., device 450. Each of such devices can contain one or more of computing device 400, 450, and an entire system can be made up of multiple computing devices 400, 450 communicating with each other.

Computing device 450 includes processor 452, memory 464, an input/output device (e.g., display 454, communication interface 466, and transceiver 468) among other components. Device 450 also can be provided with a storage device, (e.g., a microdrive or other device) to provide additional storage. Each of components 450, 452, 464, 454, 466, and 468, are interconnected using various buses, and several of the components can be mounted on a common motherboard or in other manners as appropriate.

Processor 452 can execute instructions within computing device 450, including instructions stored in memory 464. The processor can be implemented as a chipset of chips that include separate and multiple analog and digital processors. The processor can provide, for example, for coordination of the other components of device 450, e.g., control of user interfaces, applications run by device 450, and wireless communication by device 450.

Processor 452 can communicate with a user through control interface 458 and display interface 456 coupled to display 454. Display 454 can be, for example, a TFT LCD (Thin-Film-Transistor Liquid Crystal Display) or an OLED (Organic Light Emitting Diode) display, or other appropriate display technology. Display interface 456 can comprise appropriate circuitry for driving display 454 to present graphical and other data to a user. Control interface 458 can receive commands from a user and convert them for submission to processor 452. In addition, external interface 462 can communicate with processor 442, so as to enable near area communication of device 450 with other devices. External interface 462 can provide, for example, for wired communication in some implementations, or for wireless communication in other implementations, and multiple interfaces also can be used.

Memory 464 stores data within computing device 450. Memory 464 can be implemented as one or more of a computer-readable medium or media, a volatile memory unit or units, or a non-volatile memory unit or units. Expansion memory 474 also can be provided and connected to device 450 through expansion interface 472, which can include, for example, a SIMM (Single In Line Memory Module) card interface. Such expansion memory 474 can provide extra storage space for device 450, or also can store applications or other data for device 450. Specifically, expansion memory 474 can include instructions to carry out or supplement the processes described above, and can include secure data also. Thus, for example, expansion memory 474 can be provided as a security module for device 450, and can be programmed with instructions that permit secure use of device 450. In addition, secure applications can be provided through the SIMM cards, along with additional data, (e.g., placing identifying data on the SIMM card in a non-hackable manner.)

The memory can include, for example, flash memory and/or NVRAM memory, as discussed below. In one implementation, a computer program product is tangibly embodied in a data carrier. The computer program product contains instructions that, when executed, perform one or more methods, e.g., those described above. The data carrier is a computer- or machine-readable medium (e.g., memory 464, expansion memory 474, and/or memory on processor 452), which can be received, for example, over transceiver 468 or external interface 462.

Device 450 can communicate wirelessly through communication interface 466, which can include digital signal processing circuitry where necessary. Communication interface 466 can provide for communications under various modes or protocols (e.g., GSM voice calls, SMS, EMS, or MMS messaging, CDMA, TDMA, PDC, WCDMA, CDMA2000, or GPRS, among others.) Such communication can occur, for example, through radio-frequency transceiver 468. In addition, short-range communication can occur, e.g., using a Bluetooth®, WiFi, or other such transceiver (not shown). In addition, GPS (Global Positioning System) receiver module 470 can provide additional navigation- and location-related wireless data to device 450, which can be used as appropriate by applications running on device 450. Sensors and modules such as cameras, microphones, compasses, accelerators (for orientation sensing), etc. may be included in the device.

Device 450 also can communicate audibly using audio codec 460, which can receive spoken data from a user and convert it to usable digital data. Audio codec 460 can likewise generate audible sound for a user, (e.g., through a speaker in a handset of device 450.) Such sound can include sound from voice telephone calls, can include recorded sound (e.g., voice messages, music files, and the like) and also can include sound generated by applications operating on device 450.

Computing device 450 can be implemented in a number of different forms, as shown in the FIG. 16. For example, it can be implemented as cellular telephone 480. It also can be implemented as part of smartphone 482, personal digital assistant, or other similar mobile device.

Various implementations of the systems and techniques described here can be realized in digital electronic circuitry, integrated circuitry, specially designed ASICS (application specific integrated circuits), computer hardware, firmware, software, and/or combinations thereof. These various implementations can include implementation in one or more computer programs that are executable and/or interpretable on a programmable system including at least one programmable processor. The programmable processor can be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to a computer program product, apparatus and/or device (e.g., magnetic discs, optical disks, memory, Programmable Logic Devices (PLDs)) used to provide machine instructions and/or data to a programmable processor, including a machine-readable medium that receives machine instructions.

To provide for interaction with a user, the systems and techniques described here can be implemented on a computer having a device for displaying data to the user (e.g., a CRT (cathode ray tube) or LCD (liquid crystal display) monitor), and a keyboard and a pointing device (e.g., a mouse or a trackball) by which the user can provide input to the computer. Other kinds of devices can be used to provide for interaction with a user as well; for example, feedback provided to the user can be a form of sensory feedback (e.g., visual feedback, auditory feedback, or tactile feedback); and input from the user can be received in a form, including acoustic, speech, or tactile input.

The systems and techniques described here can be implemented in a computing system that includes a backend component (e.g., as a data server), or that includes a middleware component (e.g., an application server), or that includes a frontend component (e.g., a client computer having a user interface or a Web browser through which a user can interact with an implementation of the systems and techniques described here), or a combination of such back end, middleware, or frontend components. The components of the system can be interconnected by a form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

A number of systems and methods have been described. Nevertheless, it will be understood that various modifications may be made without departing from the spirit and scope of this disclosure. Accordingly, other implementations are within the scope of the following claims.

What is claimed is:

1. A system comprising:

a transducer configured to transmit a magnetic field; and a magneto-mechanical capsule comprising:

a body;

a first magnet attached to a first end of the body;

a second magnet attached to a second end of the body; and a third magnet disposed in the body between the first magnet and the second magnet, the third magnet configured to rotationally oscillate about a longitudinal axis of the body relative to the first and second magnets to produce a magnetic signal in response to the magnetic field, the magnetic signal being indicative of the rotational oscillation of the third magnet, wherein the transducer is configured to detect the magnetic signal.

2. The system of claim 1, further comprising a processor configured to determine a position or orientation of the magneto-mechanical capsule based on the detected magnetic signal.

3. The system of claim 1, wherein the transducer is configured to detect the magnetic signal after stopping the transmission of the magnetic field.

4. The system of claim 1, wherein the magnetic signal is an oscillating magnetic signal within the magnetic field that is detectable for determining a position or orientation of the magneto-mechanical capsule.

5. The system of claim 1, wherein the third magnet is disposed equidistantly between the first magnet and the second magnet.

6. The system of claim 1, further comprising a stabilizer disposed within the body, the stabilizer configured to limit a rotation of the third magnet about an axis perpendicular to the longitudinal axis.

7. The system of claim 6, wherein the stabilizer comprises (i) a first pin extending in a longitudinal direction from the third magnet and having an end that is disposed within a cavity of the first magnet and (ii) a second pin extending in an opposite longitudinal direction from the third magnet and having an end that is disposed within a cavity of the second magnet.

8. The system of claim 7, wherein the respective ends of the first and second pins are configured to move within the respective cavities of the first and second magnets in response to the magnetic field.

9. The system of claim 7, wherein the first and second pins are configured to limit the rotation of the third magnet about the axis perpendicular to the longitudinal axis by contacting respective sidewalls of the respective cavities.

10. The system of claim 6, wherein the stabilizer comprises a bushing disposed circumferentially around the third magnet or disposed around one or more stabilizing pins.

11. The system of claim 10, wherein the bushing is in slidable contact with at least one of the first magnet, the second magnet, or a sidewall of the body.

12. The system of claim 10, wherein the bushing is configured to limit the rotation of the third magnet about the axis perpendicular to the longitudinal axis by limiting an axial movement of the third magnet within the body.

13. The system of claim 1, wherein the first magnet, the second magnet, and the third magnet are at least one of disc-shaped, square, diamond-shaped, or oval-shaped.

14. The system of claim 13, wherein the first magnet, the second magnet, and the third magnet are disc-shaped and are concentrically disposed along the longitudinal axis of the body.

15. The system of claim 14, wherein the first magnet has (i) a north pole arranged on a first side of the longitudinal axis of the body and (ii) a south pole arranged on a second side of the longitudinal axis of the body.

16. The system of claim 15, wherein the north and south poles of the first magnet are arranged in the same direction as north and south poles of the second magnet.

17. The system of claim 16, wherein the north and south poles of the third magnet are arranged in an opposite direction to the north and south poles of the first and second magnets.

18. The system of claim 1, wherein the body has a length between 0.5 and 2.0 mm and a diameter between 0.1 mm and 0.8 mm.

* * * * *